(12) United States Patent  (10) Patent No.: US 8,419,796 B2
Gray, Jr. et al.  (45) Date of Patent: Apr. 16, 2013

(54) INTERVERTEBRAL PROSTHETIC SYSTEMS, DEVICES, AND ASSOCIATED METHODS

(75) Inventors: Erica M. Gray, Jr., Memphis, TN (US); Danny H. Braddock, Jr., Germantown, TN (US); Clinton R. Jacob, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 371 days.

(21) Appl. No.: 12/784,788

(22) Filed: May 21, 2010

(65) Prior Publication Data

US 2011/0288644 A1 Nov. 24, 2011

(51) Int. Cl.
*A61F 2/44* (2006.01)

(52) U.S. Cl.
USPC ............................................ 623/17.11

(58) Field of Classification Search ........... 623/17.11, 623/17.16
See application file for complete search history.

(56) References Cited

U.S. PATENT DOCUMENTS

| | | | |
|---|---|---|---|
| 6,063,121 A | 5/2000 | Xavier | |
| 6,287,308 B1 | 9/2001 | Betz et al. | |
| 6,733,531 B1 | 5/2004 | Trieu | |
| 7,588,592 B2 | 9/2009 | Winslow | |
| 8,114,162 B1 * | 2/2012 | Bradley | 623/17.16 |
| 2005/0119752 A1 * | 6/2005 | Williams et al. | 623/17.16 |
| 2005/0203512 A1 | 9/2005 | Hawkins et al. | |
| 2006/0241615 A1 | 10/2006 | Melkent | |
| 2006/0247640 A1 | 11/2006 | Blackwell | |
| 2007/0010813 A1 | 1/2007 | Zucherman et al. | |
| 2007/0233253 A1 | 10/2007 | Bray et al. | |
| 2008/0051890 A1 | 2/2008 | Waugh et al. | |
| 2008/0234826 A1 * | 9/2008 | Chappuis | 623/17.16 |
| 2008/0288072 A1 | 11/2008 | Kohm | |
| 2008/0312741 A1 | 12/2008 | Lee et al. | |
| 2009/0138087 A1 | 5/2009 | Miglietta et al. | |
| 2009/0264927 A1 | 10/2009 | Ginberg et al. | |

* cited by examiner

*Primary Examiner* — Kevin T Truong
*Assistant Examiner* — David Bates (57) ABSTRACT

Intervertebral prosthetic systems, devices, and associated methods are provided. The present disclosure provides intervertebral prosthetic devices that include lateral plates to engage the lateral walls of the vertebral bodies for stability and include a compliant central component, fusion-cage central component, or any other suitable type of motion-preserving or fusion component positioned between the lateral plates. In some instances, the lateral plates and the central component are connected by an elongated member that extends across the disc space. The designs of the present disclosure allow insertion through a unilateral approach yet still have engagement on both sides of the vertebral body to provide stability and reduce the risk of subsidence.

18 Claims, 7 Drawing Sheets

INTERVERTEBRAL PROSTHETIC SYSTEMS, DEVICES, AND ASSOCIATED METHODS

TECHNICAL FIELD

Embodiments of the present disclosure relate generally to intervertebral implants and associated methods of implantation and treatment.

BACKGROUND

Within the spine, the intervertebral disc functions to stabilize and distribute forces between vertebral bodies. It comprises a nucleus pulposus which is surrounded and confined by the annulus fibrosis. Intervertebral discs are prone to injury and degeneration. For example, herniated discs typically occur when normal wear or exceptional strain causes a disc to rupture. Degenerative disc disease typically results from the normal aging process, in which the tissue gradually loses its natural water and elasticity, causing the degenerated disc to shrink and possibly rupture. Intervertebral disc injuries and degeneration may be treated by fusion of adjacent vertebral bodies or by replacing the intervertebral disc with an implant, also known as a prosthesis or prosthetic device. Generally, fusion of the adjacent vertebral bodies prevents movement between the adjacent vertebrae. Some implants, on the other hand, preserve at least some of the range of motion provided by the natural intervertebral disc.

Although existing devices and methods associated within intervertebral implants have been generally adequate for their intended purposes, they have not been entirely satisfactory in all respects. The intervertebral prosthetic systems, devices, and associated methods of the present disclosure overcome one or more of the shortcomings of the prior art.

SUMMARY

The present disclosure provides intervertebral prosthetic systems, devices, and associated methods.

In one embodiment, an intervertebral prosthetic device is disclosed. The intervertebral prosthetic device includes a first lateral component sized and shaped for lateral insertion through a disc space between an upper vertebra and a lower vertebra from a first lateral side of a patient and into engagement with a lateral sidewall of at least one of the upper and lower vertebra on a second lateral side of the patient opposite the first lateral side. The device also includes a second lateral component sized and shaped for lateral insertion from the first lateral side of the patient and into engagement with a lateral sidewall of at least one of the upper and lower vertebra on the second lateral side of the patient. An elongated member extends between the first lateral component and the second lateral component. The elongated member is sized to extend across the disc space between the upper vertebra and the lower vertebra when the first lateral component is engaged with the lateral sidewall on the second lateral side of the patient and the second lateral component is engaged with the lateral sidewall on the first lateral side of the patient. A central component is engaged with the elongated member and positioned between the first lateral component and the second lateral component. The central component is sized and shaped for positioning in the disc space between the upper vertebra and the lower vertebra.

In some embodiments, the elongated member extends through a bore in the central component. The elongated member is movably attached to at least one of the first and second lateral components in some instances. In that regard, in some embodiments each end of the elongated member is fixedly attached to an anchor piece that is movably received within a cavity of the first and second lateral components. The anchor piece is translatable relative to the first and second lateral components within a plane defined by the cavity in some instances. In some embodiments, the first lateral component includes a first upper piece and a first lower piece, where the first upper piece movably connected to the first lower piece. In that regard, the first upper piece is pivotable and/or translatable relative to the first lower piece. Further, in some instances the lateral components each include a central portion formed of a first material and two end portions formed of a second material. In some embodiments, the first material is a resiliently flexible material (e.g., silicone, polyurethane, and other resiliently flexible materials) and the second material is more rigid than the first material (e.g., a variety of surgical-grade materials, including but not limited to stainless steel, titanium alloy, PEEK, cobalt chrome alloy, and other metal, ceramic, polymer, and/or composite materials). In some embodiments, the second lateral component includes at least one opening for receiving at least one bone anchor for fixedly securing the second lateral component to the lateral sidewall on the first lateral side of the patient.

In another embodiment, a prosthetic system is disclosed. The system includes a first component sized and shaped for lateral insertion through a disc space between an upper vertebra and a lower vertebra from a first lateral side of a patient and into engagement with lateral sidewalls the upper and lower vertebra on a second lateral side of the patient. The first component is configured to be passed through the disc space in an insertion orientation relative to the upper and lower vertebrae and transitioned into an engagement orientation relative to the upper and lower vertebrae. The engagement orientation is substantially perpendicular to the insertion orientation in some instances. The system includes a second component sized and shaped for lateral insertion from the first lateral side of the patient and into engagement with lateral sidewalls of the upper and lower vertebra on the first lateral side of the patient. The system also includes a central component positioned between and in communication with the first and second components. The central component is sized and shaped for positioning in the disc space between the upper vertebra and the lower vertebra such that an upper surface of the central component engages an endplate of the upper vertebra and a lower surface of the central component engages an endplate of the lower vertebra.

In some embodiments, the prosthetic system further includes an elongated member extending between the first component and the second component and extending through a portion of the central component. The elongated member is sized to extend across the disc space between the upper vertebra and the lower vertebra when the first component is engaged with the lateral sidewalls of the upper and lower vertebra on the second lateral side of the patient and the second component is engaged with the lateral sidewalls of the upper and lower vertebra on the first lateral side of the patient. The elongated member is movably attached to the first and second components in some instances. In that regard, the elongated member is fixedly attached to an anchor piece that is movably received within a cavity of each of the first and second components in some embodiments. The first and second components are each comprised of an upper piece and a lower piece that are translatable and pivotable relative to one another in some instances. In that regard, in some instances the lower pieces each include a projection and the upper pieces each include an elongated opening, where the projections of the lower pieces are received within the elongated openings of the upper pieces to facilitate the relative translation and pivoting of the upper and lower pieces.

In another embodiment, a surgical method is disclosed. The method includes inserting a first lateral component through a disc space between an upper vertebra and a lower vertebra from a first lateral side of a patient in an insertion orientation relative to the upper and lower vertebrae and rotating the first lateral component from the insertion orientation to an engagement orientation, where the engagement orientation is substantially perpendicular to the insertion orientation. The method also includes engaging the first lateral component in the engagement orientation with a lateral sidewall of at least one of the upper and lower vertebrae on a second lateral side of the patient opposite the first lateral side. Further, the method includes inserting a disc component into the disc space between the upper and lower vertebrae and engaging a second lateral component with a lateral sidewall of at least one of the upper and lower vertebrae on the first lateral side of the patient.

In some instances, inserting the disc component comprises advancing the disc component over an elongated member extending from the first lateral component. The method also includes engaging the elongated member with the second lateral component in some embodiments. Finally, in some embodiments engaging the second lateral component with the lateral sidewall of at least one of the upper and lower vertebrae on the first lateral side of the patient includes passing at least one bone anchor through at least one opening in the second lateral component and into the lateral sidewall of at least one of the upper and lower vertebrae on the first lateral side of the patient.

Other features and advantages of the present disclosure will become apparent from the detailed description of the illustrative embodiments of the accompanying drawings.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 1:
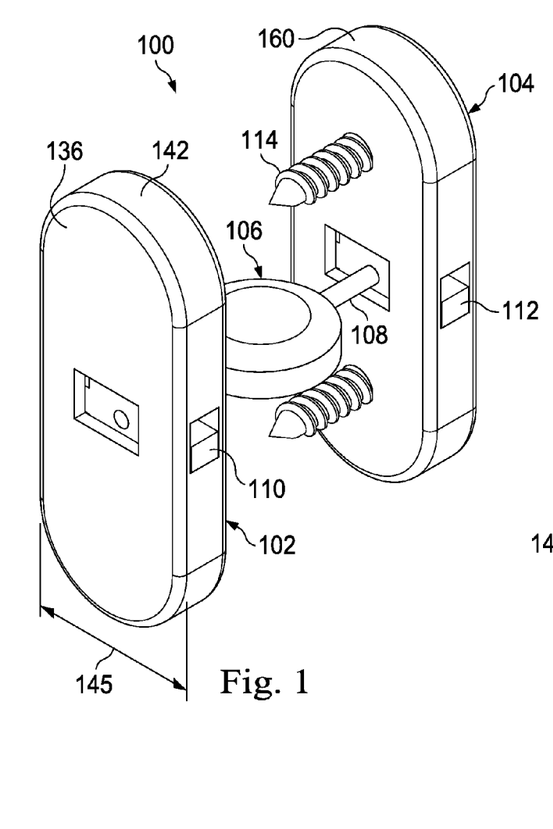
FIG. 1 is a perspective view of an intervertebral prosthetic device according to one embodiment of the present disclosure.
Figure 2:
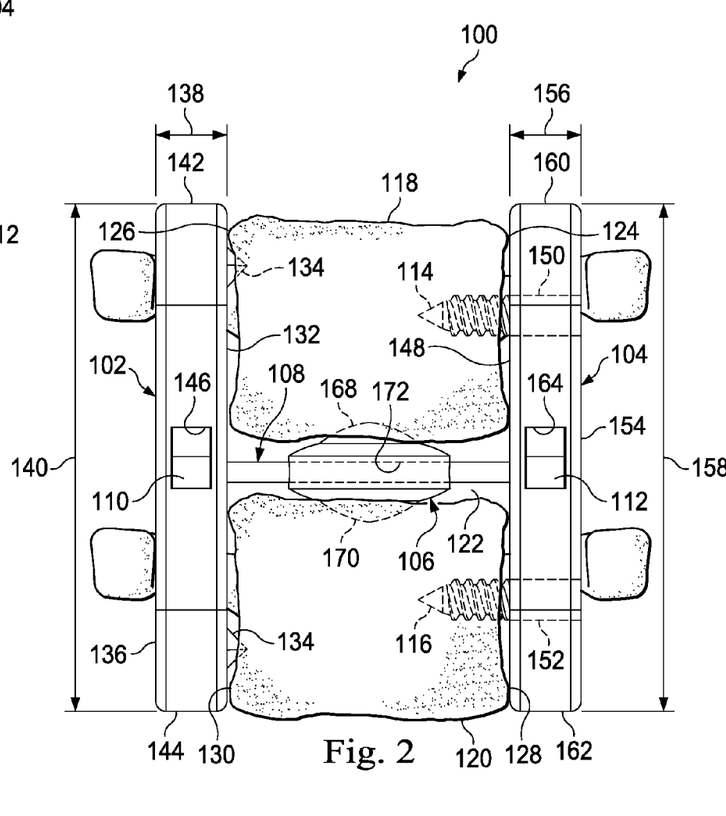
FIG. 2 is a side view of the intervertebral prosthetic device of FIG. 1 illustrating the device relative to a pair of vertebrae after implantation.
Figure 3:
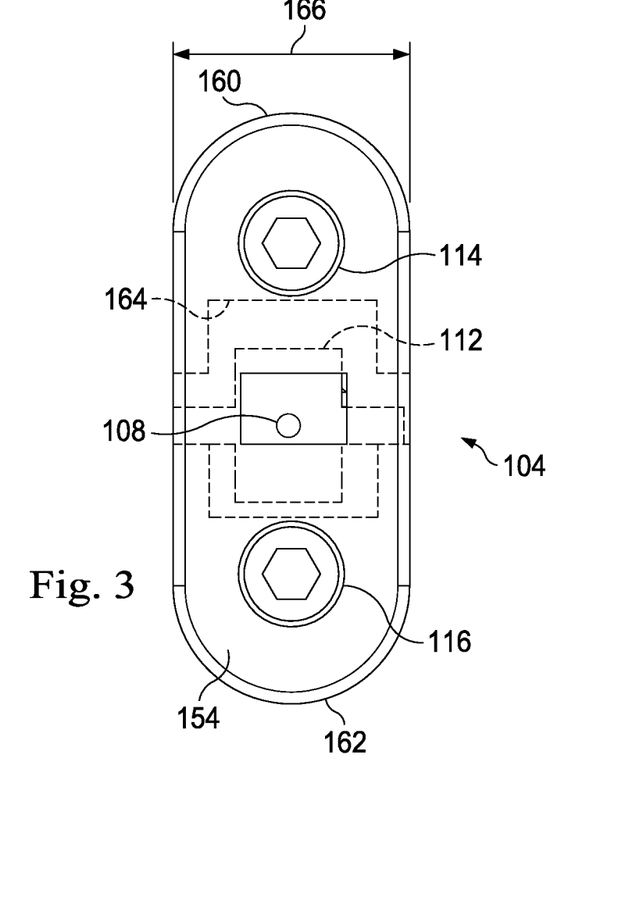
FIG. 3 is an end view of the intervertebral prosthetic device of FIGS. 1 and 2.

Referring to FIGS. 1, 2, and 3, shown therein is an intervertebral prosthetic device 100 according to one embodiment of the present disclosure. In particular, FIG. 1 is a perspective view of the intervertebral prosthetic device 100, FIG. 2 is a side view of the device relative to a pair of vertebrae after implantation, and FIG. 3 is an end view of the device.

The device 100 includes a lateral component 102, a lateral component 104, and a central component 106. The device 100 also includes an elongated member 108 extending between the lateral components 102, 104. In that regard, the ends of the elongated member 108 are secured to anchor pieces or inserts 110, 112 that are received within the lateral components 102, 104, respectively. As discussed below, the lateral components 102, 104 are configured to securely engage with lateral surfaces of adjacent vertebrae on opposite sides of the vertebrae, while the central component or core 106 is positioned within a disc space between the vertebrae. In that regard, in the illustrated embodiment the device 100 includes a pair of bone anchors 114, 116 for securing lateral component 104 to the vertebrae.

Referring more specifically to FIG. 2, the device 100 is illustrated in an implanted state relative to an upper vertebra 118 and a lower vertebra 120. As shown, between the upper and lower vertebrae 118, 120 is a disc space 122. In some instances, at least a portion of the natural disc is removed (e.g., discectomy) to create the disc space 122 between the upper and lower vertebrae 118, 120. As shown, the upper vertebra 118 includes a lateral sidewall 124 on a first lateral side and a second lateral sidewall 126 on a second lateral side that is substantially opposite the first lateral side. Similarly, the lower vertebra 120 includes a lateral sidewall 128 on the first lateral side and a lateral sidewall 130 on the second lateral side.

The lateral component 102 includes an inner surface 132 configured for engagement with the lateral sidewalls 126, 130 of the first and second vertebrae 118, 120 that are on the second lateral side. In that regard, the inner surface 132 includes engagement features 134 to encourage secure engagement between the lateral component 102 and the sidewalls 126, 130. It is understood that the inner surface 132 may include any number or type of engagement features and/or surface treatments to facilitate secure engagement with the sidewalls 126, 130. The illustrated engagement features 134 are shown simply to demonstrate the use of engagement features and should not be considered to limit the type or number of engagement features utilized.

The lateral component 102 includes an outer surface 136 opposite the inner surface 132. In that regard, the lateral component 102 has a thickness 138 between the inner surface 132 and the outer surface 136. In some instances, the thickness 138 is between about 2 mm and about 8 mm and, in some particular instances, is between about 4 mm and about 6 mm. In the illustrated embodiment the thickness 138 is substantially constant along the length of the lateral component 102. However, in other embodiments the thickness is variable along the length of the lateral component 102.

Figure 4:
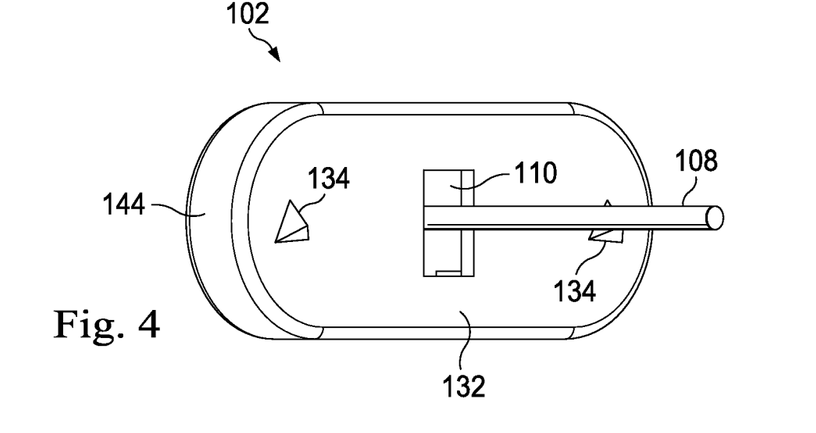
FIG. 4 is a perspective view of an arrangement illustrating implantation of a first component of a prosthetic device in an insertion orientation according to one embodiment of the present disclosure.
Figure 5:
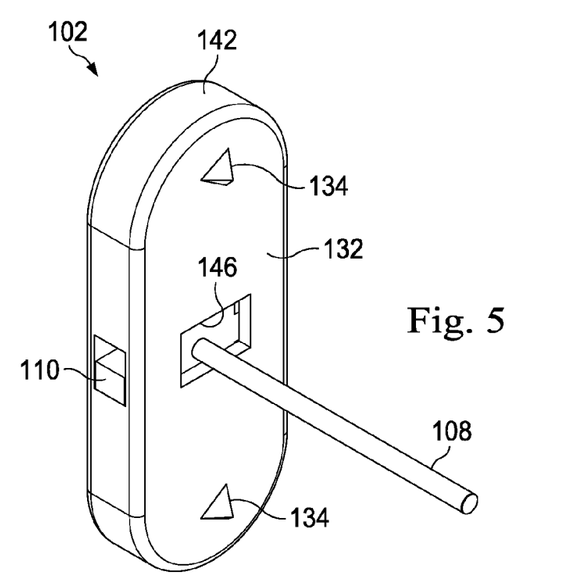
FIG. 5 is a perspective view of the arrangement of FIG. 4 illustrating the first component of the prosthetic device in an anchoring orientation.

The lateral component 102 has a height 140 between an upper end 142 and a lower end 144. In some instances, the height 140 is between about 10 mm and about 60 mm and, in some particular instances, is between about 15 mm and about 50 mm. Generally, the height 140 of the lateral component 102 is less than or equal to the length of the disc space 122 in an anterior to posterior direction but greater than the height of the disc space 122 between the vertebrae 118, 120 such that the lateral component 102 can be inserted through the disc space 122 in a horizontal position (as shown in FIG. 4) and then rotated to a vertical position (as shown in FIG. 5) after passing through the disc space. In other embodiments, the height 140 of the lateral component 102 is larger than the length of the disc space 122 in the anterior to posterior direction. In an alternative embodiment, the lateral component 102 is approximately half of the length illustrated in FIG. 2 such that it engages with only one of the vertebrae 118, 120.

As shown in FIG. 1, the lateral component 102 has a width 145. In some instances, the width 145 is between about 8 mm and about 40 mm and, in some particular instances, is between about 10 mm and about 30 mm. Generally, the width 145 is less than or equal to the height of the disc space 122 between the vertebrae 118, 120 such that the lateral component 102 can be inserted through the disc space 122 in a horizontal position (as shown in FIG. 4) and then rotated to a vertical position (as shown in FIG. 5) after passing through the disc space. It is understood that, in some instances, the vertebrae 118, 120 are distracted to increase the height of the disc space 122 to facilitate passage of the lateral component 102 through the disc space.

Referring to FIGS. 1 and 2, the lateral component 102 also includes a cavity 146 that receives the anchor piece 110. In the illustrated embodiment, the cavity 146 is larger than the anchor piece 110 received therein such that the anchor piece is movable relative to the lateral component 102. In some instances, the anchor piece is translatable relative to the lateral component 102 in a plane defined by the cavity 146. In some embodiments, the plane defined by the cavity 146 is substantially parallel to the inner and outer surfaces 132, 136 of the lateral component 102. In some instances, the cavity 146 and anchor piece 110 have a structural relationship substantially similar to or identical to the structural relationship of the lateral component 104 and anchor piece 112 that is described in greater detail below with respect to FIG. 3.

Referring again to FIG. 2, the lateral component 104 includes an inner surface 148 configured for engagement with the lateral sidewalls 124, 128 of the first and second vertebrae 118, 120 that are on the first lateral side. In that regard, the lateral component 104 includes openings 150, 152 extending between the inner surface 148 and an outer surface 154 that facilitate passage of bone anchors 114, 116 through the lateral component 104 and into secure engagement with the sidewalls 124, 128 of the vertebrae 118, 120. It is understood that the inner surface 148 may include additional and or alternative types of engagement features and/or surface treatments to facilitate secure engagement with the sidewalls 124, 128. Further, it is understood that the bone anchors 114, 116, which are illustrated as being bone screws, may be any suitable type of bone anchor (e.g., staples, pins, etc.) for securing the lateral component 104 to the sidewalls 124, 128 of the vertebrae 118, 120. The illustrated bone anchors 114, 116 are shown to demonstrate the use of bone anchors and should not be considered to limit the type or number of bone anchors utilized.

The lateral component 104 has a thickness 156 between the inner surface 148 and the outer surface 154. In some instances, the thickness 156 is between about 2 mm and about 20 mm and, in some particular instances, is between about 4 mm and about 12 mm. In the illustrated embodiment the thickness 156 is substantially constant along the length of the lateral component 104. However, in other embodiments the thickness is variable along the length of the lateral component 104. The lateral component 104 has a height 158 between an upper end 160 and a lower end 162. In some instances, the height 158 is between about 10 mm and about 60 mm and, in some particular instances, is between about 15 mm and about 50 mm. Generally, the height 158 of the lateral component 104 is greater than the height of the disc space 122 between the vertebrae 118, 120 so that the lateral component 104 can be securely engaged with the sidewalls 124, 128 of the vertebrae. However, in an alternative embodiment, the lateral component 104 is approximately half of the length illustrated in FIG. 2 such that it engages with only one of the vertebrae 118, 120. As shown in FIG. 3, the lateral component 104 has a width 166. In some instances, the width 166 is between about 8 mm and about 40 mm and, in some particular instances, is between about 10 mm and about 30 mm.

In some instances, the lateral components 102, 104 have substantially similar outer profiles such that at least the heights 140, 158 and widths 145, 166 are substantially equal between the two components. However, in other embodiments the lateral components 102, 104 have different outer profiles such that the heights 140, 158 and/or widths 145, 166 are different between the two components. In that regard, in some instances the height 158 and/or width 166 of the lateral component 104 is greater than the height 140 and/or width 145 of the lateral component 102 since the lateral component 104 does not need to be passed through the disc space 122.

The lateral component 104 also includes a cavity 164 that receives the anchor piece 112. As best seen in FIG. 3, the cavity 164 has a larger profile than the anchor piece 112 received therein such that the anchor piece is movable relative to the lateral component 102 within the cavity. As shown, the anchor piece 112 is translatable relative to the lateral component 104 in a plane defined by the cavity 164 that is substantially parallel to the inner and outer surfaces 148, 154 of the lateral component. In that regard, the anchor piece 112 is able to translate left and right as well as up and down relative to the lateral component 104 as viewed in FIG. 3. It is understood that the particular structural features of the cavity 164 and anchor piece 112 are for exemplary purposes only and in no way limit the types of cavities or anchor pieces that may be utilized. In that regard, it is understood that various types of engagements between the anchor pieces 110, 112 and the lateral components 102, 104 are utilized in other embodiments. For example, in some embodiments the structural features limit translation of the anchor component to a single direction (e.g., only translation up and down or only translation left and right as view in FIG. 3). In other embodiments, the structural features allow the anchor component to pivot or be angled relative to the lateral component.

Referring again to FIG. 2, the central component 106 includes an upper surface 168 for mating with an endplate of the upper vertebra 118 and a lower surface 170 for mating with an endplate of the lower vertebra 120. The central component 106 also includes an opening 172 for receiving the elongated member 108. In the illustrated embodiment the opening 172 extends through the central component from a first lateral side to an opposing second lateral side. In the illustrated embodiment the central component 106 is a compliant core. In some instances, the compliant core is formed of resiliently flexible materials that replicate the function of the natural disc. Suitable materials for the compliant core include but are not limited to polymers such as silicone, polyurethane, and other resiliently flexible materials. In other embodiments, the central component 106 is a fusion-cage or other similar fusion device designed to encourage fusion between the upper and lower vertebrae 118, 120.

The lateral components 102, 104 can be made from a variety of surgical-grade materials, including but not limited to stainless steel, titanium alloy, PEEK, cobalt chrome alloy, and other metal, ceramic, polymer, and/or composite materials. In some embodiments, the elongated member 108 is formed of flexible materials, including but not limited to polymers such as silicone, polyurethane, and other resiliently flexible materials. In other embodiments, the elongated member 108 is formed of more rigid materials, including but not limited to stainless steel, titanium alloy, PEEK, cobalt chrome alloy, and other metal, ceramic, polymer, and/or composite materials. Similarly, the anchor pieces 110, 112 are formed of resiliently flexible materials (including but not limited to polymers such as silicone, polyurethane, and other resiliently flexible materials) in some embodiments and formed of more rigid materials (including but not limited to stainless steel, titanium alloy, PEEK, cobalt chrome alloy, and other metal, ceramic, polymer, and/or composite materials) in other embodiments.

Figure 6:
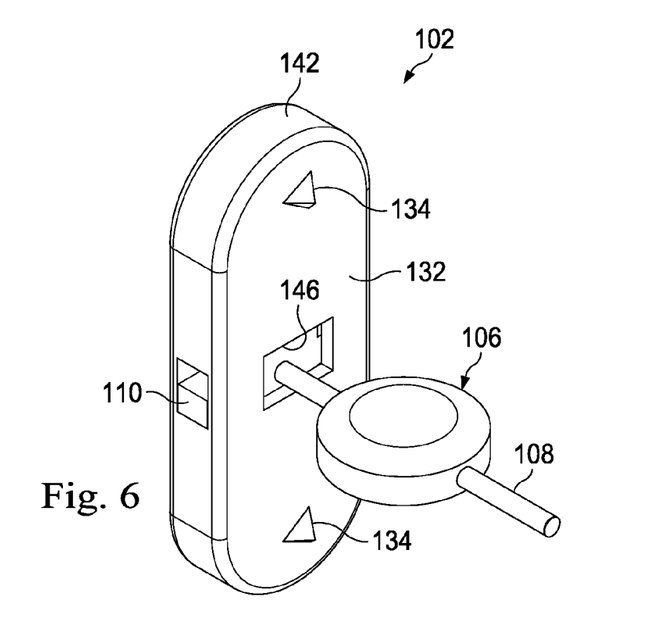
FIG. 6 is a perspective view of the arrangement of FIGS. 4 and 5 illustrating a central component of the prosthetic device being positioned over an elongated member of the prosthetic device extending from the first component according to one embodiment of the present disclosure.
Figures 7, 8:
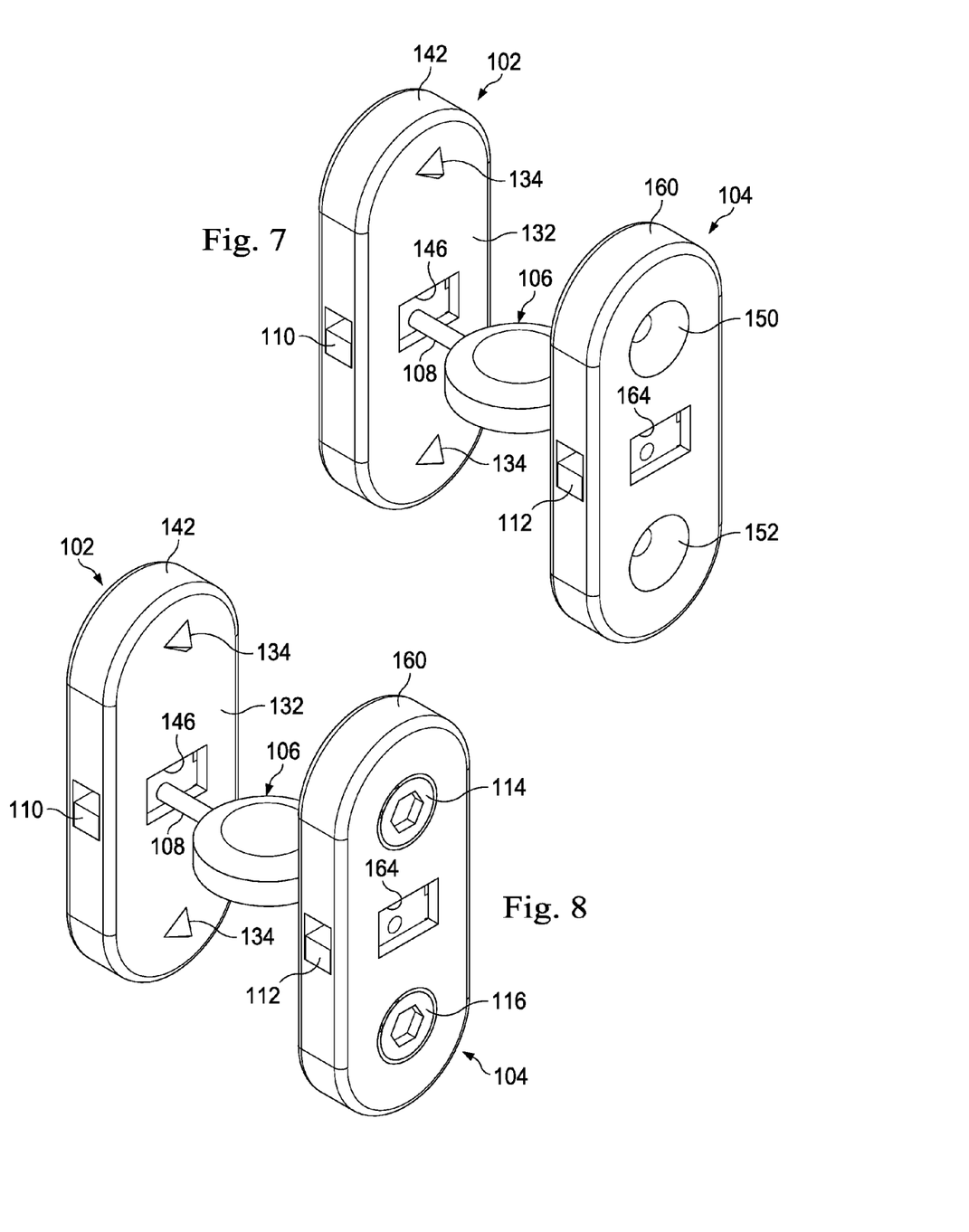
FIG. 7 is a perspective view of the arrangement of FIGS. 4, 5, and 6 illustrating implantation of a second component of the prosthetic device.
FIG. 8 is a perspective view of the arrangement of FIGS. 4, 5, 6, and 7 illustrating the prosthetic device in a fully implanted configuration with bone anchors extending through the second component of the prosthetic device.

Referring now to FIGS. 4, 5, 6, 7, and 8 shown therein are aspects of a method implanting an intervertebral prosthetic device in accordance with the present disclosure. In particular, FIG. 4 is a perspective view of the lateral component 102 of the prosthetic device 100 in an insertion orientation; FIG. 5 is a perspective view similar to FIG. 4 but illustrating the lateral component 102 in an anchoring orientation; FIG. 6 is a perspective view similar to FIGS. 4 and 5 illustrating the central component 106 of the prosthetic device being positioned over the elongated member 108 extending from the lateral component 102; FIG. 7 is a perspective view similar to FIGS. 4, 5, and 6 illustrating implantation of the lateral component 104 of the prosthetic device 100; and FIG. 8 is a perspective view similar to FIGS. 4, 5, 6, and 7 illustrating the prosthetic device 100 in a fully implanted configuration with bone anchors 114, 116 extending through the lateral component 104 of the prosthetic device 100.

Referring more specifically to FIG. 4, the lateral component 102 is inserted between the upper vertebra 118 and the lower vertebra 120 in an insertion configuration. More specifically, the lateral component 102 is laterally inserted into the intervertebral disc space 122 between the upper and lower vertebrae 118, 120. In that regard, a discectomy or other procedure for removing all or a portion of the natural disc between the upper and lower vertebrae 118, 120 is performed to create the intervertebral disc space 122 to allow insertion of the lateral component 102. As shown, in the insertion configuration of FIG. 4 the lateral component 102 is oriented in a generally horizontal direction such that upper and lower ends 142, 144 are positioned in an anterior-to-posterior orientation. In the insertion orientation, the lateral component 102 has a maximum height that is less than the distance between the endplates of the upper and lower vertebrae 118, 1120. In that regard, the insertion configuration allows the lateral component 102 to be laterally inserted through the disc space 122 to a position adjacent the lateral sidewalls 126, 130 of the upper and lower vertebra 118, 120 opposite from the insertion point. In the illustrated embodiment of FIG. 2, for example, the insertion point is on the left lateral side of the patient (right side of the drawing) the lateral component 102 is passed through the disc space 122 to a position adjacent the right lateral sidewalls (left side of the drawing). It is understood that in other embodiments the insertion is from the right lateral side of the patient. Further, it is understood that the lateral insertion is either a direct lateral insertion or an oblique lateral insertion.

Referring more specifically to FIG. 5, after the lateral component 102 has been inserted through the disc space 122 the lateral component 102 is rotated to an anchoring configuration. As shown, in the anchoring configuration of FIG. 5 the lateral component 102 is oriented in a generally vertical direction such that the upper and lower ends 142, 144 are positioned in a super-to-inferior orientation. In the illustrated embodiment, the lateral component 102 is rotated approximately 90 degrees between the insertion configuration and the anchoring configuration. Rotation of the lateral component 102 is accomplished utilizing any suitable surgical tool. In some instances, a surgical tool engages the opening in the inner surface 132 defined by the cavity 146. In that regard, the tool utilized to insert the lateral component 102 can also be utilized to rotate the lateral component between the insertion and anchoring configurations.

In the anchoring configuration a portion of the inner surface 132 of the lateral component 102 adjacent the upper end 142 engages the sidewall 126 of the upper vertebra 118 while a portion of the inner surface 132 adjacent the lower end 144 engages the sidewall 130 of the lower vertebra 120. In that regard, the lateral component 102 is sized such that it spans across the disc space 122 between the vertebrae 118, 120 in the anchoring configuration. In some instances, a plurality of lateral components of varying sizes (e.g., lengths and/or widths) are provided and medical personnel selects the appropriate sized lateral component 102 based on the anatomy of the patient.

Referring to FIG. 6, the central component 106 is inserted over the elongated member 108 extending from the lateral component 102. In some embodiments, the elongated member 108 and/or the central component 106 include features that facilitate engagement of the central component 106 at a particular location along the length of the elongated member 108. For example, in some instances the elongated member 108 includes one or more projections that are configured for engagement with corresponding recesses within surfaces of the central component 106 defining the opening 172 such that engagement of the projection(s) and recess(es) holds the central component 106 in a fixed position along the length of the elongated member. In other instances, the central component 106 is allowed to translate along the length of the elongated member 108 after implantation. For example, in some instances the upper and lower surfaces 168, 170 of the central component 106 are shaped such that the central component is self-centering relative to the upper and lower vertebrae 118, 120. That is, while the central component 106 will move about the disc space 122 between the vertebrae 118, 120, the shape of the central component 106 results in the central component naturally returning to a desired, centralized location within the disc space.

Referring now to FIG. 7, with the central component 106 positioned over the elongated member 108 the lateral component 104 is engaged with the free end of the elongated member. In that regard, in some instances the elongated member 108 is secured to the anchor piece 112 that is positioned within the cavity 164 of the lateral component 104. In some embodiments, the elongated member 108 is passed through an opening in the anchor piece 112 and secured to the anchor piece by crimping, gluing, fastening, or otherwise fixedly attaching the elongated member to the anchor piece. In some instances, the elongated member 108 is pulled through the anchor piece 112 with sufficient tension to encourage fixed engagement of the lateral component 102 with the sidewalls 126, 130. Excess portions of the elongated member 108 are cut off in some instances such that the elongated member does not extend beyond the lateral component 104. Referring to FIG. 8, with the lateral component 104 positioned adjacent to the lateral surfaces 124, 128 of the upper and lower vertebrae 118, 120, the bone anchors 114, 116 are inserted through the openings 150, 152 and into engagement with the upper and lower vertebrae.

In other instances, the intervertebral prosthetic device 100 is assembled (i.e., lateral components 102, 104, central component 106, and elongated member 108 are assembled together) prior to implantation. In that regard, the entire device 100 may be inserted in an insertion configuration and then rotated to an anchoring configuration after the lateral component 102 passes through the disc space. Alternatively, with the device 100 assembled the lateral component 102 can be positioned in the insertion configuration illustrated in FIG. 4, inserted through the disc space 122, and then rotated to the anchoring configuration illustrated in FIG. 5.

As noted above, in alternative embodiments, either one or both of the lateral components 102, 104 is sized such that it engages with only one of the vertebrae 118, 120. Such embodiments can allow greater range of motion between the vertebrae 118, 120 as compared to the lateral components 102, 104 that engage both vertebrae.

As shown, the prosthetic devices and associated methods of the present disclosure facilitate lateral insertion of intervertebral prosthetic devices from a single side of the patient. More specifically, the devices and methods of the present disclosure require access from a single lateral direction, but still facilitate secure engagement of the prosthetic devices with both lateral sides of the vertebrae. Further, a direct lateral approach for lumbar spine surgery offers many benefits. For example, a direct lateral approach can overcome the risks associated with an anterior approach and the space limitations of a posterior approach.

Figure 9:
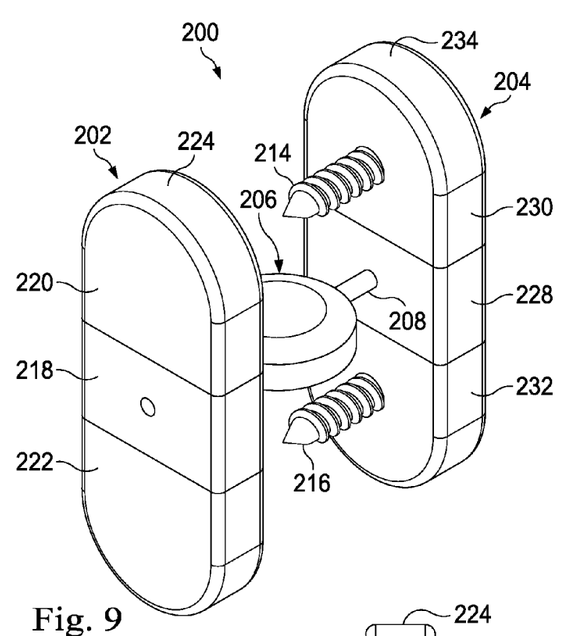
FIG. 9 is a perspective view of an intervertebral prosthetic device according to another embodiment of the present disclosure.
Figure 10:
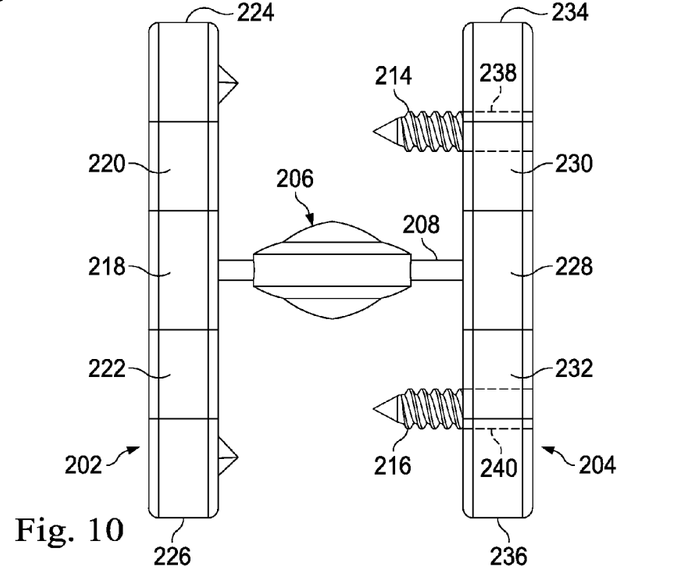
FIG. 10 is a side view of the intervertebral prosthetic device of FIG. 9.

Referring now to FIGS. 9 and 10, shown therein is an alternative embodiment of an intervertebral prosthetic device 200 according to the present disclosure. In that regard, FIG. 9 is a perspective view of the prosthetic device 200 and FIG. 10 is a side view of the prosthetic device 200. As shown, the prosthetic device 200 includes a lateral component 202, a lateral component 204, and a central component 206. The device 200 also includes an elongated member 208 extending between the lateral components 202, 204. The lateral components 202, 204 are configured to securely engage with lateral surfaces of adjacent vertebrae 118, 120 on opposite sides of the vertebrae, while the central component or core 106 is positioned within the disc space 122 between the vertebrae. In that regard, in the illustrated embodiment the device 200 includes a pair of bone anchors 214, 216 for securing lateral component 204 to the sidewalls 124, 128 of the vertebrae 118, 120.

The lateral component 202 includes a central portion 218 bounded by an upper portion 220 and a lower portion 222. The upper portion 220 extends between the central portion 218 and an upper end 224 of the lateral component 202, while the lower portion 222 extends between the central portion 218 and a lower end 226. Similarly, the lateral component 204 includes a central portion 228 bounded by an upper portion 230 and a lower portion 232. The upper portion 230 extends between the central portion 228 and an upper end 234 of the lateral component 204, while the lower portion 232 extends between the central portion 228 and a lower end 236. The upper portion 230 includes an opening 238 and the lower portion 232 includes an opening 240 for receiving the bone anchors 214, 216, respectively.

In the embodiment of FIGS. 9 and 10, the central portions 218, 228 are formed of a resiliently flexible material such that the lateral components 202, 204 allow at least some motion between the vertebrae 118, 120 after implantation. In that regard, in some instances the resiliently flexible central portions 218, 228 allow movement between the vertebrae 118, 120 associated with flexion, extension, and/or rotation. In some instances, the central portions 218, 228 allow movement in one or more directions but limit or prevent movement in one or more other directions.

The upper portions 220, 230 and the lower portions 222, 232 are formed of materials having increased rigidity and/or hardness relative to the central portions 218, 228. In that regard, the increased rigidity and/or hardness of the upper and lower portions 220, 222, 230, 232 facilitate secure engagement with the upper and lower vertebrae 118, 120. In some embodiments, the upper and lower portions 220, 222, 230, 232 are formed of stainless steel, titanium carbide, cobalt chrome alloy, ceramic, PEEK, UHMWPE, and other metal, ceramic, polymer, and/or composite materials having increased rigidity relative to the central portions 218, 228.

Figure 11:
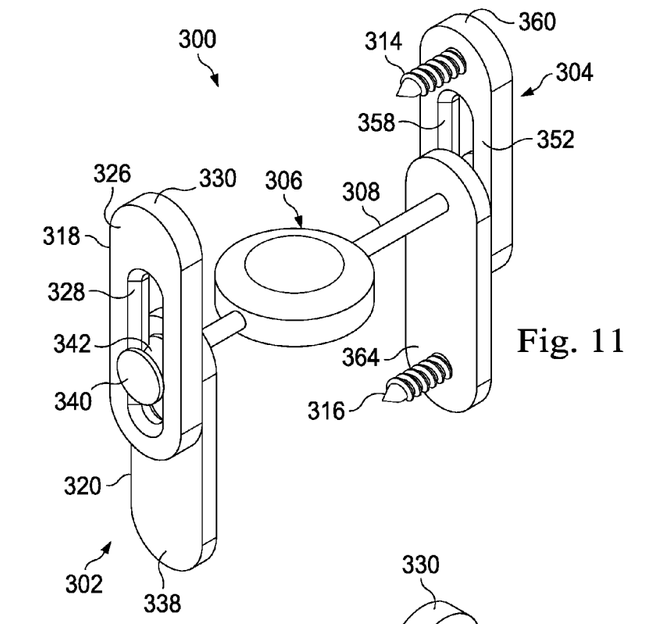
FIG. 11 is a perspective view of an intervertebral prosthetic device according to another embodiment of the present disclosure.
Figure 12:
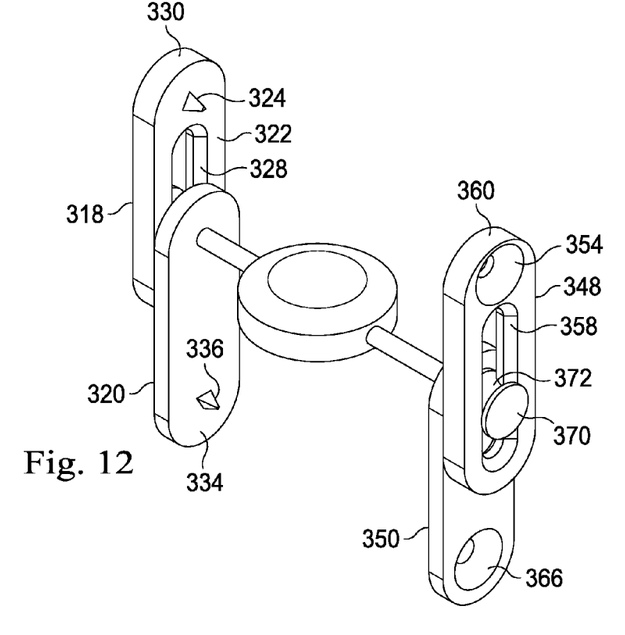
FIG. 12 is an alternative perspective view of the intervertebral prosthetic device of FIG. 11.
Figure 13:
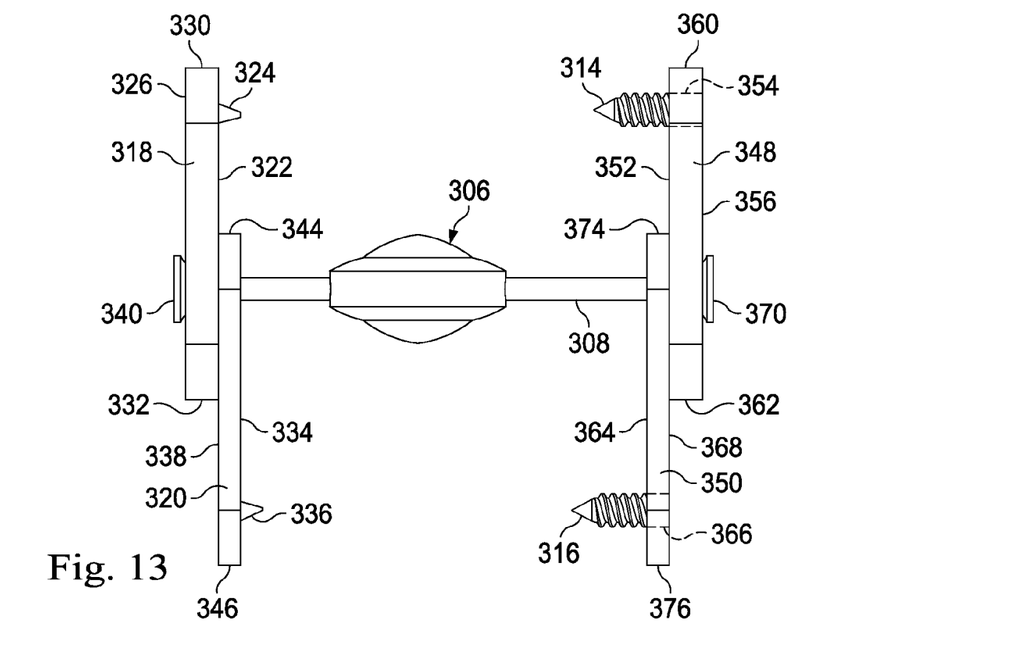
FIG. 13 is a side view of the prosthetic device of FIGS. 11 and 12.
Figure 14:
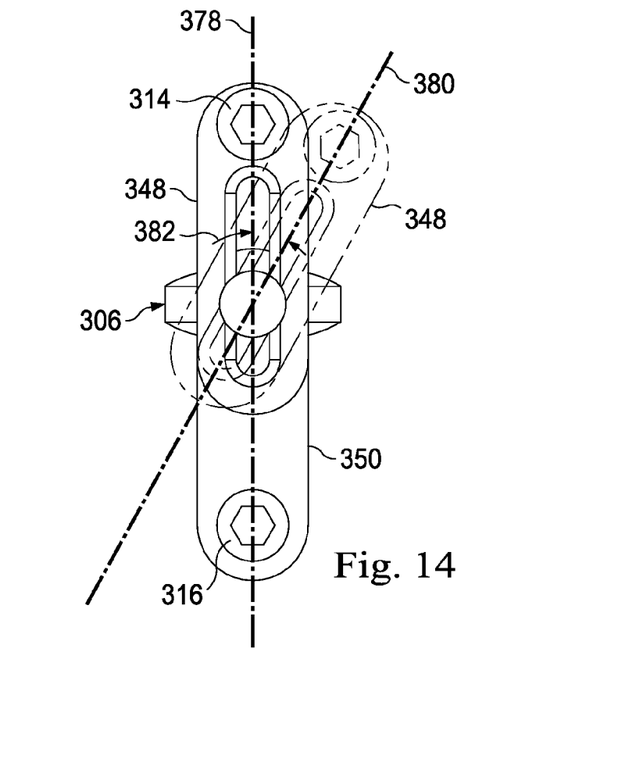
FIG. 14 is an end view of the prosthetic device of FIGS. 11, 12, and 13.

Referring now to FIGS. 11, 12, 13, and 14, shown therein is another embodiment of an intervertebral prosthetic device 300 according to the present disclosure. Specifically, FIG. 11 is a perspective view of the intervertebral prosthetic device 300; FIG. 12 is an alternative perspective view of the device; FIG. 13 is a side view of the device; and FIG. 14 is an end view of the device.

Referring more specifically to FIGS. 11, 12, and 13, the prosthetic device 300 includes a lateral component 302, a lateral component 304, and a core 306. The device 300 also includes an elongated member 308 extending between the lateral components 302, 304. The lateral components 302, 304 are configured to securely engage with lateral surfaces of adjacent vertebrae 118, 120 on opposite sides of the vertebrae, while the core 306 is positioned within the disc space 122 between the vertebrae. In that regard, in the illustrated embodiment the device 300 includes a pair of bone anchors 314, 316 for securing lateral component 304 to the sidewalls 124, 128 of the vertebrae 118, 120.

As shown, the lateral component 302 includes an upper piece 318 and a lower piece 320. As best seen in FIGS. 12 and 13, the upper piece 318 includes an inner surface 322 for engaging with the sidewall 126 of the upper vertebra 118. In that regard, the inner surface 322 includes engagement features 324 to facilitate fixed engagement of the upper piece 318 with the upper vertebra 118. As best seen in FIGS. 11 and 13, the upper piece 318 also includes an outer surface 326 opposite the inner surface 322. An elongated opening 328 extends along the length of the upper piece 318 between the inner surface 322 and the outer surface 326. In the illustrated embodiment, the surfaces defining the elongated opening 328 taper inward from both the inner surface 322 and the outer surface 326, as shown in FIGS. 11 and 12. The elongated opening 328 extends along a majority of the length of the upper component 318 between an upper end 330 and a lower end 332.

The lower piece 320 includes an inner surface 334 for engaging with the sidewall 130 of the lower vertebra 120. In that regard, the inner surface 334 includes engagement features 336 to facilitate fixed engagement of the lower piece 320 with the lower vertebra 120. As best seen in FIGS. 11 and 13, the lower piece 320 also includes an outer surface 338 opposite the inner surface 334. A projection 340 extends outward from the outer surface 338 of the lower piece 320. The projection 340 of the lower piece is received within the elongated recess 328 of the upper piece 318. In that regard, the projection 340 has an inner surface 342 that is contoured to generally match the taper of the surfaces defining elongated opening 328 such that the projection 340 is translatable and pivotable relative to the upper piece 318 within the elongated opening 328. In the illustrated embodiment, the projection 340 is positioned closer to the upper end 344 of the lower component 320 than the lower end 346. In some instances, the projection 340 is positioned along the length of the lower piece 320 between the upper end 344 and the lower end 346 such that it is substantially aligned with the disc space 122 between the vertebrae 118, 120 when the prosthetic device 300 is in a neutral position.

Referring still to FIGS. 11, 12, and 13, the lateral component 304 also includes an upper piece 348 and a lower piece 350. As best seen in FIGS. 11 and 13, the upper piece 348 includes an inner surface 352 for engaging with the sidewall 124 of the upper vertebra 118. In that regard, a bore 354 extends through the upper piece 348 from the inner surface 352 to an outer surface 356. The bore 354 is configured to receive the bone anchor 314 to facilitate fixed engagement of the upper piece 348 with the upper vertebra 118. An elongated opening 358 extends along the length of the upper piece 348 between the inner surface 352 and the outer surface 356. In the illustrated embodiment, the surfaces defining the elongated opening 358 taper inward from both the inner surface 352 and the outer surface 356, as shown in FIGS. 11 and 12. The elongated opening 358 extends along a majority of the length of the upper component 348 between an upper end 360 and a lower end 362.

The lower piece 350 includes an inner surface 364 for engaging with the sidewall 128 of the lower vertebra 120. In that regard, a bore 366 extends through the lower piece 350 from the inner surface 364 to an outer surface 368. The bore 366 is configured to receive the bone anchor 316 to facilitate fixed engagement of the lower piece 350 with the lower vertebra 120. A projection 370 extends outward from the outer surface 368 of the lower piece 350. The projection 370 of the lower piece 350 is received within the elongated recess 358 of the upper piece 348. In that regard, the projection 370 has a contoured inner surface 372 that generally matches the taper of the surfaces defining elongated opening 358 such that the projection 370 is translatable and pivotable relative to the upper piece 348 within the elongated opening 358. In the illustrated embodiment, the projection 370 is positioned closer to the upper end 374 of the lower component 350 than the lower end 376. In some instances, the projection 370 is positioned along the length of the lower piece 350 between the upper end 374 and the lower end 376 such that it is substantially aligned with the disc space 122 between the vertebrae 118, 120 when the prosthetic device 300 is in a neutral position.

Referring now to FIG. 14, as described above the engagement of the projections 340, 370 of the lower pieces 320, 350 with the elongated recesses 328, 358 of the upper pieces 318, 348 allow the upper and lower pieces to translate and pivot with respect to one another. Such relative movement will be discussed in greater detail in the context of the upper piece 348 and the lower piece 350 as shown in FIG. 14. In that regard, the upper and lower pieces 348, 350 are able translate with respect to one another along the longitudinal axis 378. Further, the upper and lower pieces 348, 350 are able to pivot with respect to one another. Generally, the projection 370 serves as the pivot point between the pieces 348, 350. In that regard, the phantom depiction of the upper piece illustrates an orientation of the upper piece 348 relative to the lower piece 350 in one pivoted position. As shown the longitudinal axis 380 of the upper piece 348 extends at an angle 382 relative to the longitudinal axis of the lower piece 350, which is represented by axis 378. It is understood that the orientation illustrated in FIG. 14 is for exemplary purposes only and is not limiting to the directions in which the pieces 348, 350 can pivot relative to one another. In that regard, it is understood that the upper piece 348 can pivot in the other direction (left as viewed in FIG. 14) relative to the lower piece 350 as well. It is also understood that both upper and lower pieces 348, 350 may pivot relative to a longitudinal axis of the spinal column.

The engagement of the projection 370 with the elongated recess 358 can limit the amount of angulation or pivot allowed between the pieces 348, 350. In some embodiments, the maximum angulation allowed between the pieces 348, 350 is 45 degrees or less in either direction. Engagement of the projection 370 with the elongated recess 358 also limit the amount of translation allowed between the pieces 348, 350. In that regard, the length and/or the positioning of the elongated recess 358 on the upper piece 348 in combination with the size and/or the positioning of the projection 370 on the lower piece 350 are utilized to define the amount of translation permitted between the upper and lower pieces 348, 350.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the embodiment. In that regard, it is fully contemplated that generally any of the features described with respect to one of the prosthetic devices above may be combined with features of one or more of the other prosthetic devices described above. Further, it is understood that embodiments described has having upper and lower components and/or left and right components and/ or other similar directional components are inverted in some instances such that the upper component becomes the lower component and vice versa and/or features of the upper component become features of the lower component and vice versa. Accordingly, it is appropriate that the appended claims be construed broadly and in a manner consistent with the scope of the present disclosure.

What is claimed is:
1. An intervertebral prosthetic device comprising:
a first lateral component sized and shaped for lateral insertion through a disc space between an upper vertebra and a lower vertebra from a first lateral side of a patient and into engagement with a lateral sidewall of at least one of the upper and lower vertebra on a second lateral side of the patient opposite the first lateral side;

a second lateral component sized and shaped for lateral insertion from the first lateral side of the patient and into engagement with a lateral sidewall of at least one of the upper and lower vertebra on the first lateral side of the patient;

an elongated member extending between and connected to each of the first lateral component and the second lateral component, the elongated member sized to extend across the disc space between the upper vertebra and the lower vertebra when the first lateral component is engaged with the lateral sidewall of at least one of the upper and lower vertebra on the second lateral side of the patient and the second lateral component is engaged with the lateral sidewall of at least one of the upper and lower vertebra on the first lateral side of the patient; and a central component directly engaged with the elongated member and positioned between the first lateral component and the second lateral component, the central component sized and shaped for positioning in the disc space between the upper vertebra and the lower vertebra;

wherein the first lateral component includes a central portion positioned between two end portions, the central portion formed of a first material and the two end portions formed of a second material different than the first material, the first material being resiliently flexible and the second material being more rigid than the first material.

2. The intervertebral prosthetic device of claim 1, wherein the elongated member extends through a bore in the central component.

3. The intervertebral prosthetic device of claim 1, wherein the elongated member is movably attached to at least one of the first and second lateral components.

4. The intervertebral prosthetic device of claim 3, wherein the elongated member is fixedly attached to an anchor piece that is movably received within a cavity of at least one of the first and second lateral components.

5. The intervertebral prosthetic device of claim 4, wherein the anchor piece is movably received within at least one of the first and second lateral components such that the anchor piece is translatable relative to the at least one of the first and second lateral components within a plane defined by the cavity.

6. The intervertebral prosthetic device of claim 1, wherein the end portions of the first lateral component include a first upper end portion and a first lower end portion, the first upper end portion movably connected to the first lower end portion.

7. The intervertebral prosthetic device of claim 6, wherein the first upper end portion is pivotable relative to the first lower end portion.

8. The intervertebral prosthetic device of claim 7, wherein the first upper end portion is translatable relative to the first lower end portion.

9. The intervertebral prosthetic device of claim 1, wherein the second lateral component includes at least one opening for receiving at least one bone anchor for fixedly securing the second lateral component to the lateral sidewall of at least one of the upper and lower vertebra on the first lateral side of the patient.

10. A prosthetic system comprising:

a first component sized and shaped for lateral insertion through a disc space between an upper vertebra and a lower vertebra from a first lateral side of a patient and into engagement with lateral sidewalls of the upper and lower vertebra on a second lateral side of the patient opposite the first lateral side of the patient, the first component configured to be passed through the disc space in an insertion orientation relative to the upper and lower vertebrae and transitioned into an engagement orientation relative to the upper and lower vertebrae, the engagement orientation being substantially perpendicular to the insertion orientation;

a second component sized and shaped for lateral insertion from the first lateral side of the patient and into engagement with lateral sidewalls of the upper and lower vertebra on the first lateral side of the patient;

a central component positioned between and in communication with the first and second components, the central component sized and shaped for positioning in the disc space between the upper vertebra and the lower vertebra such that an upper surface of the central component engages an endplate of the upper vertebra and a lower surface of the central component engages an endplate of the lower vertebra; and an elongated member extending between the first component and the second component and extending through a portion of the central component, the elongated member sized to extend across the disc space between the upper vertebra and the lower vertebra when the first component is engaged with the lateral sidewalls of the upper and lower vertebra on the second lateral side of the patient and the second component is engaged with the lateral sidewalls of the upper and lower vertebra on the first lateral side of the patient.

11. The intervertebral prosthetic device of claim 10, wherein the elongated member is movably attached to the first and second components.

12. The intervertebral prosthetic device of claim 11, wherein the elongated member is fixedly attached to an anchor piece that is movably received within a cavity of each of the first and second components.

13. The intervertebral prosthetic device of claim 10, wherein the first component includes a first upper piece and a first lower piece, the first upper piece translatable and pivotable relative to the first lower piece; and wherein the second component includes a second upper piece and a second lower piece, the second upper piece translatable and pivotable relative to the second lower piece.

14. The prosthetic system of claim 13, wherein the first lower piece and the second lower piece each include a projection and wherein the first upper piece and the second upper piece each include an elongated opening, the projections of the first lower piece and the second lower piece being received within the elongated openings of the first upper piece and the second upper piece.

15. A surgical method comprising:

providing the implant of claim 1;

inserting the first lateral component through a disc space between an upper vertebra and a lower vertebra from a first lateral side of a patient in an insertion orientation relative to the upper and lower vertebrae;

rotating the first lateral component from the insertion orientation to an engagement orientation, the engagement orientation being substantially perpendicular to the insertion orientation;

engaging the first lateral component in the engagement orientation with a lateral sidewall of at least one of the upper and lower vertebrae on a second lateral side of the patient opposite the first lateral side;

inserting the central component into the disc space between the upper and lower vertebrae; and engaging the second lateral component with a lateral sidewall of at least one of the upper and lower vertebrae on the first lateral side of the patient.

16. The surgical method of claim 15, wherein inserting the central component comprises advancing the component over the elongated member.

17. The surgical method of claim 16, further comprising engaging the elongated member with the second lateral component.

18. The surgical method of claim 16, wherein engaging the second lateral component with the lateral sidewall of at least one of the upper and lower vertebrae on the first lateral side of the patient includes passing at least one bone anchor through at least one opening in the second lateral component and into the lateral sidewall of at least one of the upper and lower vertebrae on the first lateral side of the patient.

* * * * *